United States Patent [19]

Hofer et al.

[11] 4,065,288
[45] Dec. 27, 1977

[54] NOVEL 2-CHLOROETHANE-(THIONO)-PHOSPHONIC ACID AMIDO COMPOUNDS AND PLANT GROWTH INHIBITING COMPOSITIONS

[75] Inventors: Wolfgang Hofer, Wuppertal-Vohwinkel; Reinhard Schliebs, Cologne; Robert Schmidt, Leverkusen; Ludwig Eue, Cologne, all of Germany

[73] Assignee: Bayer Aktiengesellschaft, Leverkusen, Germany

[21] Appl. No.: 626,514

[22] Filed: Oct. 28, 1975

Related U.S. Application Data

[60] Continuation of Ser. No. 413,134, Nov. 5, 1973, abandoned, which is a division of Ser. No. 119,912, March 1, 1971, Pat. No. 3,825,635.

[30] Foreign Application Priority Data

Mar. 4, 1970 Germany .............................. 2010119

[51] Int. Cl.$^2$ .............................................. A01N 5/00
[52] U.S. Cl. .......................................... 71/76; 71/71; 71/77; 71/78; 71/86; 71/87
[58] Field of Search ............................... 71/86, 87, 76

[56] References Cited

U.S. PATENT DOCUMENTS

| | | | |
|---|---|---|---|
| 3,010,986 | 11/1961 | Reetz | 71/86 |
| 3,114,761 | 12/1963 | Price et al. | 71/87 |
| 3,551,528 | 12/1970 | Randall | 71/86 |
| 3,644,600 | 2/1972 | Beriger | 71/86 |
| 3,679,780 | 7/1972 | Randall et al. | 71/86 |
| 3,825,635 | 7/1974 | Hofer et al. | 71/87 |
| 3,879,188 | 4/1975 | Fritz et al. | 71/86 |
| 3,901,679 | 8/1975 | Hofer et al. | 71/87 |

Primary Examiner—Glennon H. Hollrah
Attorney, Agent, or Firm—Burgess, Dinklage & Sprung

[57] ABSTRACT

Certain novel 2-chloroethane-(thiono)-phosphonic acid amido compounds of the formula

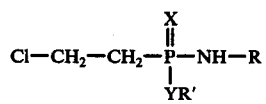

in which
X and Y, which may be the same or different, are oxygen or sulfur,
R is hydrogen or alkyl, and
R' is alkyl, or, if R is hydrogen or Y is sulfur,
R' may additionally be phenyl which may be substituted by hydroxy, (lower) alkyl, halogen or nitro possess marked plant growth regulant properties, e.g., selective herbicidal activity, growth promoting and growth altering properties.

15 Claims, No Drawings

NOVEL 2-CHLOROETHANE-(THIONO)-PHOSPHONIC ACID AMIDO COMPOUNDS AND PLANT GROWTH INHIBITING COMPOSITIONS

This application is a continuation of Ser. No. 413,134 filed Nov. 5, 1973, now abandoned, which in turn is a divisional application of Ser. No. 119,912, filed Mar. 1, 1971, now U.S. Pat. No. 3,852,635.

The present invention relates to certain novel 2-chloroethane-(thiono)-phosphonic acid amido compounds, to plant growth regulant compositions containing them, and to their use as plant growth regulating agents.

It is known from Netherlands Patent Specification No. 6,802,633 that 2-chloroethanephosphonic acid exhibits plant-growth-regulating properties.

Surprisingly, it has now been found that certain 2-chloroethane-(thiono)-phosphonic acid amido compounds according to the invention show a notably greater plant-growth-regulating activity than the 2-chloroethanephosphonic acid known from the prior art, which may be regarded as the structurally closest art compound having the same type of activity. The substances according to the invention therefore represent a valuable enrichment of the art.

The compounds of present invention are 2-chloroethane-(thiono)-phosphonic acid amido compounds of the general formula

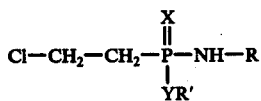

in which
X and Y, which may be the same or different, are oxygen or sulfur,
R is hydrogen or alkyl, e.g., lower alkyl, and
R' is alkyl, e.g., lower alkyl, or, if R is hydrogen or Y is sulfur, R' may additionally be phenyl which may be substituted by hydroxy, (lower) alkyl, halogen or nitro.

R is preferably hydrogen or alkyl with 1 to 4 carbon atoms. R' is preferably alkyl with 1 to 4 carbon atoms or a phenyl radical substituted by nitro, methyl, hydroxy and/or chlorine.

These compounds exhibit strong plant-growth-regulating properties.

The present invention also provides a process for the production of a 2-chloroethane-(thiono)-phosphonic acid amido compound of the formula (I) in which
a. a 2-chloroethane-(thiono)-phosphonic acid amide chloride of the general formula

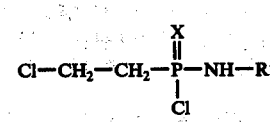

in which X has the meaning stated above and R" is alkyl, preferably with 1 to 4 carbon atoms, is reacted with a compound of the general formula

in which Y and R' have the meanings stated above, (the compound of the formula (III) may optionally be used in the form of its alkali metal salt, alkaline earth metal salt or ammonium salt), optionally in the presence of an acid-binding agent, and optionally in the presence of a solvent, or b. a 2-chloroethane-(thiono)-phosphonic acid ester halide of the general formula

in which X, Y and R' have the meaning stated above, and Hal is halogen (preferably chlorine or bromine), is reacted with a compound of the general formula

in which R has the meaning stated above, optionally in the presence of an acid-binding agent and optionally in the presence of a solvent.

If 2-chloroethanephosphonic acid N-monomethylamide chloride and p-chlorothiophenol are used as starting materials, the reaction course according to process variant (a) can be represented by the following formula scheme:

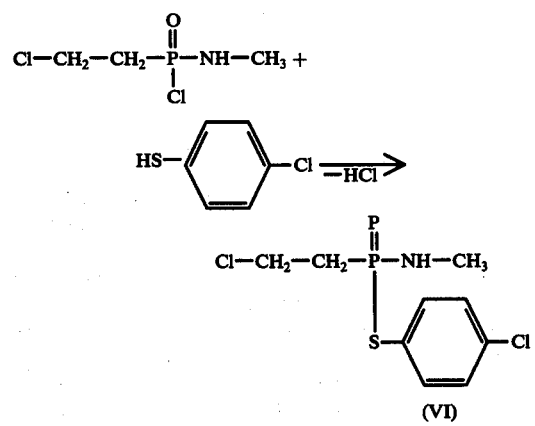

If 2-chloroethanethionophosphonic acid phenyl ester chloride and ammonia are used as starting materials, the reaction course according to process variant (b) can be represented by the following formula scheme:

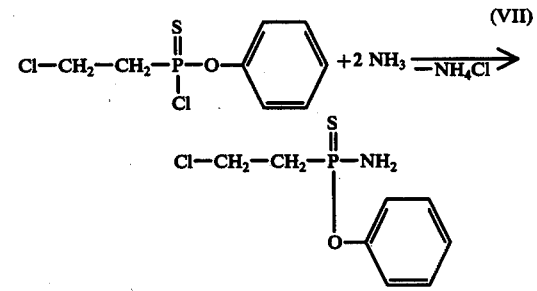

The starting materials are defined generally by the formulae (II) to (V).

As examples of the amines of the formula (V), alcohols, mercaptans, phenols and thiophenols of the formula (III), there are mentioned in particular:
ammonia, methyl, ethyl, propyl and n-, sec.-, tert.- or iso-butyl amine, methanol, ethanol, propanol and n-, sec.-, tert.- or iso-butyl alcohol, methyl, ethyl, propyl, iso-propyl and butyl mercaptan, 2-,3- and 4-chlorophenol, 2-, 3- and 4-nitrophenol, 2-, 3- and 4-methylphenol as well as resorcinol, catechol and hydroquinone, thiophenol, o-, m-, p-thiocresol and 2- and 4-chlorothiophenol.

The amines, alcohols, mercaptans, phenols and thiophenols used as starting materials are known and can be prepared according to known methods.

The 2-chloroethane-(thiono)-phosphonic acid ester chlorides or amido chlorides of the formulae (IV) or (II), respectively, used as starting materials are not known but can be obtained in simple manner according to known methods by reaction of 2-chloroethane-(thiono)-phosphonic acid dichloride with amines, alcohols, mercaptans phenols or thiophenols (the phenols and thiophenols possibly being used in the form of their alkali metal salts, alkaline earth metal salts or ammonium salts), optionally in the presence of an acid-binding agent and optionally, in the presence of a solvent, at temperatures from $-10°$ to $+50°$ C.

Examples (a) to (d) set forth below illustrate this process:

EXAMPLE a

Preparation of 2-chloroethanethionophosphonic acid N-monomethyl amide chloride

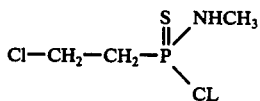

15.5 g (0.5 mole) methylamine in 200 ml toluene are added to 49.5 g (0.25 mole) 2-chloroethanethionophosphonic acid dichloride in 500 ml toluene. Stirring was afterwards effected for one hour at room temperature; the salts were then filtered off with suction, washing with water and drying over sodium sulfate are effected, and the solvent was drawn off. After slight distillation at 0.01 mm Hg/80° C, a yellow oil remained behind. Yield: 41 g (85%) 2-chloroethanethionophosphonic acid N-monomethyl amide chloride, $n_D^{28} = 1.5613$.

Analysis: Calculated for $C_3H_8Cl_2NPS$: S, 16.65% N, 7.30%. Found: S, 16.47% N, 7.35%.

EXAMPLE b

Preparation of 2-chloroethanethionephosphonic acid phenyl ester chloride

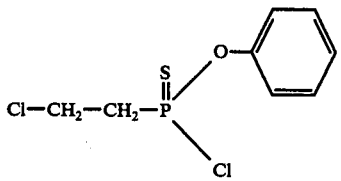

19 g (0.2 mole) phenol in 50 ml $H_2O$ and 8 g (0.2 mole) sodium hydroxide are added to 39.5 g (0.2 mole) 2-chloroethanethionophosphonic acid dichloride at 20° C. Stirring for 2 hours at room temperature was afterwards effected, followed by taking up in methylene chloride, separation of the organic phase and washing with water. After drying over sodium sulfate had been carried out, the solvent was drawn off and slight distillation (1 mm Hg/60° C) was then effected. Yield: 39 g (77%) 2-chloroethanethionophosphonic acid phenyl ester chloride as colourless liquid, $n_D^{28} = 1.5688$.

Analysis: Calculated for $C_8H_9Cl_2OPS$: S, 12.55%; Cl, 27.90%. Found: S, 12.46%; Cl, 28.82%.

EXAMPLE c

Preparation of 2-chloroethanephosphonic acid N-monoisopropylamide chloride

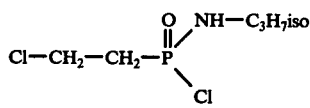

59 g (1 mole) iso-propylamine are added to 91 g (0.5 mole) 2-chloroethanephosphonic acid dichloride in 1.5 l of toluene at 0° C. Stirring was afterwards effected for 1 hour at room temperature, the salts were filtered off with suction, the solution was washed with a little water and the solvent was drawn off with suction; slight distillation was then effected (0.01 mm Hg/80° C). Yield: 93 g (91%) 2-chloroethanephosphonic acid N-monoisopropylamide chloride; $n_D^{28} = 1.4854$.

Analysis: Calculated for $C_5H_{12}Cl_2NOP$: N, 6.85%; Cl, 34.80%. Found: N, 6.58%; Cl, 33.74%.

EXAMPLE d

Analogously with Example c, there is prepared 2-chloroethane-phosphonic acid N-mono-methylamide chloride

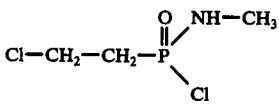

Yield: 56% $n_D^{28} = 1.5019$.

To obtain the compounds of the present invention, as indicated above, either process variant according to the present invention may be carried out in the presence of a solvent (this term includes a mere diluent). The solvent may for example be water or an inert organic solvent. Such solvents include aliphatic and aromatic (possibly chlorinated) hydrocarbons such as benzene, toluene, xylene, benzine, methylene chloride, chloroform, carbon tetrachloride, chlorobenzene; ethers, such as diethyl ether, dibutyl ether, dioxan; ketones, such as acetone, methylethyl ketone, methylisopropyl ketone, methylisobutyl ketone; and nitriles, such as acetonitrile.

An acid-binding agent may be used, as mentioned above. All customary acid-binding agents are suitable. Particularly suitable are alkali metal carbonates and alcoholates, such as sodium and potassium carbonate and sodium and potassium methylate or ethylate; and aliphatic, aromatic or heterocyclic amines, such as triethylamine, dimethylaniline, dimethylbenzylamine and pyridine.

The reaction temperatures can be varied within a fairly wide range. In general, the work is carried out at from $-20°$ to 100° C, preferably 0° to 60°.

The reactions are generally carried out at normal pressure.

When carrying out the process variants according to the invention, approximately 1 mole of alcohol, mercaptan, phenol or thiophenol and approximately 1 mole of acid acceptor used per mole of (thiono) phosphonic acid amide chloride; approximately 2 moles of primary amine or ammonia are used per mole of (thiono) phosphonic acid ester chloride. The reactions may be carried out in water or another suitable solvent, in most cases at room temperature. A slight excess of the compounds of formulae (III) and (V) is not detrimental.

Working up may take place according to customary methods. The substances according to the invention are obtained in most cases in the form of colourless to slightly yellow-coloured, viscous, water-insoluble oils which cannot be distilled without decomposition but can, by so-called "slight distillation" (that is, by longer heating to moderately elevated temperatures under vacuum), be freed from the last volatile components and can in this way be purified. For their characterization, the refractive index is especially useful. If the compounds are obtained in crystalline form, the melting point serves for their characterization.

The following examples are illustrative:

EXAMPLE 1

Preparation of 2-chloroethanephosphonic acid isopropyl ester N-monoisopropylamide

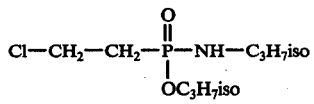

24 g (0.4 mole) isopropanol and 33 g (0.33 mole) triethylamine are added to 67 g (0.33 mole) 2-chloroethanephosphonic acid N-monoisopropylamide chloride in 200 ml benzene at room temperature. Stirring was afterwards effected for 2 hours at 50° C, followed by suction filtration from precipitated salt, and the reaction solution was washed with water. After drying with sodium sulfate and drawing off the solvent, slight distillation was effected. There remained behind a colourless oil, $n_D^{22} = 1.4686$, yield: 50 g (67%) 2-chloroethanephosphonic acid isopropyl ester N-monoisopropylamide.

Analysis: Calculated for $C_8H_{19}ClNO_2P$: 15.65% Cl; 6.15% N. Found: 16.05% Cl; 6.36% N.

The 2-chloroethane-phosphonic acid N-mono-isopropylamide chloride used as starting product was prepared from 2-chloroethane-phosphonic acid dichloride and iso-propylamine in toluene at 0° C. Yield: 91% of the theory, $n_D^{28} = 1.4854$.

EXAMPLE 2

Preparation of 2-chloroethanephosphonic acid ethyl ester N-monoisopropylamide

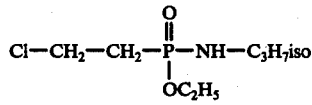

87 ml (0.2 mole) ethanolic sodium ethylate solution are added to 41 g (0.2 mole) 2-chloroethanephosphonic acid N-monoisopropylamide chloride in 200 ml benzene at room temperature. Stirring was afterwards effected for 2 hours; the salts were then filtered off with suction, the reaction solution was washed with water, and drying with sodium sulfate was effected. After the solvent had been drawn off, slight distillation was carried out. There remained behind a colourless oil, $n_D^{26} = 1.4580$, yield: 27 g (64%) 2-chloroethanephosphonic acid ethyl ester N-monoisopropylamide.

Analysis: Calculated for $C_7H_{17}ClNO_2P$: 16.65% Cl; 6.60% N. Found: 16.33% Cl; 6.56% N.

Starting Product compare Example 1.

EXAMPLE 3

Preparation of 2-chloroethanethiophosphonic acid S-ethyl ester N-monoisopropylamide

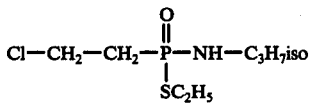

13 g (0.2 mole) ethylmercaptan and 20 g (0.2 mole) triethylamine are added to 41 g (0.2 mole) 2-chloroethanephosphonic acid N-monoisopropylamide chloride in 100 ml benzene. Stirring was afterwards effected for 2 hours at 40° C; the salts were then filtered off with suction, the reaction solution was washed with water, and drying with sodium sulfate was carried out. After the solvent had been drawn off, there remained behind a crystalline residue, m.p. 51° C, yield: 15 g (33%) 2-chloroethanethiophosphonic acid S-ethyl ester N-monoisopropylamide.

Analysis: Calculated for $C_7H_{17}ClNOPS$: 15.45% Cl; 6.10% N; 13.95% S. Found: 15.30% Cl; 6.08% N; 13.80% S.

Starting product compare Example 1.

EXAMPLE 4

Preparation of 2-chloroethane-thio-phosphonic acid S-phenyl ester N-monoisopropylamide

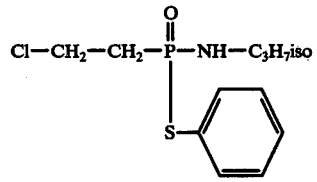

was prepared analogously with Example 3, m.p. 61° C, yield: 59% 2-chloroethane-thio-phosphonic acid S-phenyl ester N-monoisopropylamide.

Analysis: Calculated for $C_{11}H_{17}ClNOPS$: 5.50% N; 11.50% S. Found: 5.55% N; 11.95% S.

EXAMPLE 5

Preparation of 2 chloroethanethionophosphonic acid phenyl ester amide

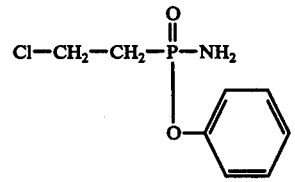

To 51 g (0.2 mole) 2-chloroethanethionophosphonic acid phenyl ester chloride, emulsified in 100 ml of water, there are added, at room temperature, 30 g (0.42 mole) of aqueous ammonia solution. Stirring was afterwards effected for 2 hours; the organic phase was then taken up in methylene chloride, washing with water was effected and, after drying with sodium sulfate had been carried out, the solvent was drawn off. After slight distillation, there remained behind a pale oil, $n_D^{27} = 1.5848$, yield: 32 g (68%) 2-chloroethanethionophosphonic acid phenyl ester amide.

Analysis: Calculated for $C_8H_{11}ClNOPS$: 15.05% Cl; 5.95% N; 12.60% S. Found: 14.82% Cl; 5.21% N; 12.42% S.

The starting product used was prepared from 2-chloroethanethiono-phosphonic acid dichloride and sodium phenolate in water, $n_D^{28} = 1.5688$, yield: 77% 2-chloroethanethiono-phosphonic acid phenyl ester chloride.

EXAMPLE 6

Preparation of 2-chloroethanethionophosphonic acid 4'-chlorophenyl ester amide

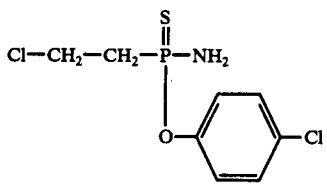

87 g (0.3 mole) 2-chloroethanethionophosphonic acid 4'-chlorophenyl ester chloride in 500 ml benzene are treated with gaseous ammonia at room temperature until the solution was saturated with ammonia. Stirring was afterwards effected for one hour; the salt was then filtered off with suction, and the reaction solution was washed with water. After drying with sodium sulfate, the solvent was drawn off. After slight distillation, there remained behind a colourless oil, $n_D^{24} = 1.5945$, yield: 62 g (76%) 2-chloroethanethionophosphonic acid 4'-chlorophenyl ester amide.

Analysis: Calculated for $C_8H_{10}Cl_2NOPS$: 26.15% Cl; 5.17% N; 11.85% S. Found: 26.23% Cl; 4.83% N; 11.65% S.

The starting product was prepared analogously with the starting product of Example 5, $n_D^{23} = 1.5856$, yield: 59% 2-chloroethane-thiono-phosphonic acid 4'-chlorophenyl ester chloride.

EXAMPLE 7

Preparation of 2-chloroethane-thiono-phosphonic acid 2',4'-dichloro-phenyl ester amide

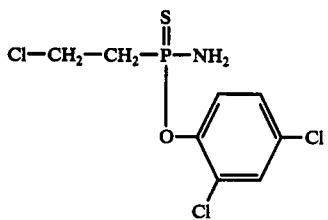

was prepared analogously with Example 6, $n_D^{24} = 1.6020$, yield: 86%.

Analysis: Calculated for $C_9H_{11}Cl_3NOPS$: 35.00% Cl; 10.5% S. Found: 35.54% Cl; 10.1% S.

The starting product was prepared analogously with the starting product of Example 5, $n_D^{20} = 1.5962$, yield: 60% 2-chloroethane-thiono-phosphonic acid 2',4'-dichloro-phenyl ester chloride.

The 2-chloroethane (thiono) phosphonic acid derivatives of this invention interfere with the physiological phenomena of plant growth and can therefore be used as plant growth regulators.

The different effects of these active compounds depend essentially on the point in time of the application, with reference to the development stage of the seed or the plant, as well as on the concentrations applied.

Plant growth regulators are used for various purposes which are connected with the development stage of the plants. Thus, with plant growth regulators the seed germination can either be inhibited or promoted, depending on the concentration applied. This inhibition or promotion relates to the seedling development.

The bud dormancy of the plants, that is to say the endogenic annular cycle, can be influenced by the active compounds, so that the plants may for example shoot or blossom at a point in time at which they normally show no readiness to shoot or blossom.

The shoot or root growth can be promoted or inhibited by the active compounds in manner dependent on concentration. Thus, it is possible for example to inhibit very strongly the growth of the fully formed plant, or to bring the plant as a whole to a more robust habitus or to produce a dwarf growth.

An example of an economic application is the suppression of grass growth at roadsides and waysides. Further, the growth of lawns can be inhibited by growth regulators, so that the frequency of grass-cutting (of lawn-mowing) can be reduced.

During the growth of the plant, the branching to the side can be multiplied by a chemical breaking of the apical dominance. This can be a valuable feature for example in the case of propagation of plants by cuttings. In concentration-dependent manner, however, it is also possible to inhibit the growth of side-shoots, for example in tobacco plants in order to prevent the formation of side-shoots after decapitation and thus to promote the leaf growth.

In the case of the influencing of blossom formation, there can be achieved, in manner dependent on concentration and the time of the application, either a retarding or an acceleration of blossom formation. Under certain circumstances, a multiplication of blossom initiation can be attained, these effects occurring when the appropriate treatments are carried out at the time of the normal blossom formation.

The influence of the active compound on the foliage of the plants can be so regulated that a defoliation is achieved, for example in order to facilitate the harvest or to reduce transpiration at a time at which plants are to be transplanted.

Fruit initiation can be promoted so that more, or seedless, fruits are formed (parthenocarpy). Under certain conditions, the premature fall of fruit can also be prevented, or the fruit fall can be promoted up to a certain extent in the sense of a chemical thinning out. The promotion of the fruit fall can, however, also be so exploited that the treatment is effected at the time of the harvest, whereby harvesting is facilitated.

By spraying unripe fruits with the compounds according to the invention, the ripening process can be accelerated and a better colouring of the fruits can be achieved. The compounds can also be applied to a crop field infested with weeds to damage the weeds without substantial injury to the crops.

The active compounds according to the present invention can be converted into the usual formulations, such as solutions, emulsions, suspensions, powders, pastes and granulates. These may be produced in known manner, for example by mixing the active compounds with extenders, that is, liquid or solid diluents or carriers, optionally with the use of surface-active agents, that is, emulsifying agents and/or dispersing agents. In the case of the use of water as an extender, organic solvents can, for example, also be used as auxiliary solvents.

| Compound No. | Structure | Chemical Name |
|---|---|---|
| 1 | Cl—CH$_2$—CH$_2$—P(=O)(NH—C$_3$H$_7$-iso)(S—C$_2$H$_5$) | 2-chloroethanethiophosphonic acid-S-ethyl ester N-monoisopropylamide |
| 2 | Cl—CH$_2$—CH$_2$—P(=O)(NH—C$_3$H$_7$-iso)(S—C$_6$H$_5$) | 2-chloroethanethiophosphonic acid-S-phenyl ester N-monoisopropylamide |
| 3 | Cl—CH$_2$—CH$_2$—P(=S)(NH$_2$)(O—C$_6$H$_4$—Cl) | 2-chloroethanethionophosphonic acid-O-(4'-chlorophenyl)-ester amide |
| 4 | Cl—CH$_2$—CH$_2$—P(=O)(NH—C$_3$H$_7$-iso)(O—C$_3$H$_7$-iso) | 2-chloroethanephosphonic acid isopropyl ester N-monoisopropylamide |

As liquid diluents or carriers, there are preferably used aromatic hydrocarbons, such as xylenes or benzene, chlorinated aromatic hydrocarbons, such as chlorobenzenes, paraffins, such as mineral oil fractions, alcohols, such as methanol or butanol, or strongly polar solvents, such as dimethyl formamide or dimethyl sulfoxide, as well as water.

As solid diluents or carriers, there are preferably used ground natural minerals, such as kaolins, clays, talc or chalk, or ground synthetic minerals, such as highly-dispersed silicic acid or silicates.

Preferred examples of emulsifying agents include nonionic and anionic emulsifiers, such as polyoxyethylene-fatty acid esters, polyoxyethylene-fatty alcohol ethers, for example alkylarylpolyglycol ethers, alkyl sulfonates and aryl sulfonates; and preferred examples of dispersing agents include lignin, sulfite waste liquors and methyl cellulose.

The formulations contain, in general, from 0.1 to 95, preferably 0.5 to 90, percent by weights of active compound.

The active compounds may be applied as such or in the form of their formulations or of the application forms prepared therefrom, such as ready-to-use solutions, emulsifiable concentrates, emulsions, suspensions, spray powders, pastes, soluble powders, dusting agents and granulates. Application may take place in the usual manner, for example by watering, squirting, spraying, scattering, dusting, etc.

The concentrations of active compound can be varied within a fairly wide range for actual application. In general, concentrations of 0.0005 to 2% by weight, preferably from 0.01 to 0.5%, are used.

There are applied, in general, 0.1 to 100 kg, preferably 1 to 10 kg, of active compound per hectare of soil area.

As regards the application time, there is generally a preferred space of time for application, depending on the object to be achieved, and on the climatic and vegetative circumstances.

The growth influencing characteristics of the compounds of this invention are illustrated by the following Examples.

The following compounds were tested:

EXAMPLE A

Growth inhibition/linseeds

Solvent: 40 parts by weight acetone
Emulsifier: 0.25 part by weight alkylaryl polyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Batches of 25 linseeds are laid out on 2 filter papers in a Petri dish. 10 ml of the preparation of active compound are pipetted into each dish. Germination of the seeds takes place in the dark at 25° C.

After three days, the length of the shoot was determined and the growth inhibition compared with the control plant was expressed as a percentage. 100% denotes the standstill of growth, and 0% denotes a growth corresponding to that of the untreated plant.

The active compounds, the concentration of the active compound in ppm (-mg/kg) and results can be seen from Table A.

Table A

| | Growth inhibition / linseeds | |
|---|---|---|
| | % inhibition of the shoot with | |
| Active Compound | 50 ppm | 250 ppm |
| water (control) | 0 | 0 |
| Cl—CH$_2$—CH$_2$—P(=O)(OH)(OH) (known) | 15 | 36 |
| Compound 1 | 70 | 82 |
| Compound 2 | 80 | 85 |

EXAMPLE B

Growth inhibition and defoliation/beans

Solvent: 40 parts by weight acetone
Emulsifier: 0.25 part by weight alkylarylpolyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Beans (Phaseolus vulgaris) 10 cm high are sprayed with preparations which contain 5000 ppm of active compound. After 6 days, the average length and the number of leaves of 3 beans per experiment were evaluated.

The results can be seen from Table B.

Table B

| Growth inhibition and defoliation / beans | | |
|---|---|---|
| Active Compound | Length in cm with 5000 ppm | Number of leaves with 5000 ppm |
| water (control) | 17.0 | 6 |
| 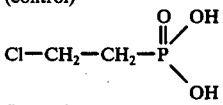 (known) | 11.0 | 4 |
| Compound 3 | 10.5 | 0 |

EXAMPLE C

Growth inhibition/tomato plants

Solvent: 40 parts by weight acetone
Emulsifier: 0.25 part by weight alkylarylpolyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Tomato plants of a height of 10 cm were sprayed with a preparation which contained 500 ppm of active compound.

After 8 days, the percentage inhibition of the treated plants compared with the untreated control plant was determined. With 100% inhibition, no growth was present; with 0% inhibition, the growth corresponds to that of the control plant.

The active compounds, concentration of active compound in ppm (-mg/kg) and the results can be seen from Table C.

Table C

| Growth inhibition / tomatoes | |
|---|---|
| Active Compound | % inhibition with 500 ppm |
| water (control) | 0 |
| 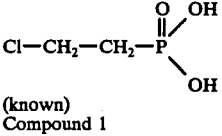 (known) | 43 |
| Compound 1 | 66 |

Table C-continued

| Growth inhibition / tomatoes | |
|---|---|
| Active Compound | % inhibition with 500 ppm |
| Compound 2 | 48 |

EXAMPLE D

Growth inhibition/apple seedlings

Solvent: 40 parts by weight acetone
Emulsifier: 0.25 part by weight alkylarylpolyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Apple seedlings are, at a height of about 2 cm, sprayed with a preparation which contains 500 ppm of active compound. After 7 days, the percentage inhibition of the treated plants compared with the untreated control plant was determined. With 100% inhibition, no growth was present; with 0% inhibition, the growth corresponds to that of the control plant.

Table D shows the results.

Table D

| Growth inhibition / apple seedlings | |
|---|---|
| Active Compound | % inhibition with 500 ppm |
| water (control) | 0 |
| 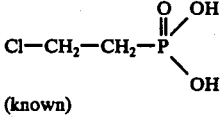 (known) | 25 |
| Compound 2 | 32 |

EXAMPLE E

Growth inhibition/Cynosurus

Solvent: 40 parts by weight acetone
Emulsifier: 0.25 part by weight alkylarylpolyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

A grass planting (Cynosurus cristatus) was sprayed with a preparation (which contained 1000 ppm of active compound) in an applied amount of 25 kg/hectare. After 14 days, the retardation of grass growth was determined and expressed in % compared with the untreated control.

The results can be seen from Table E.

Table E

| Growth inhibition / Cynosurus | |
|---|---|
| Active Compound | % inhibition |
| water (control) | 0 |

Table E-continued

| Growth inhibition / Cynosurus | |
|---|---|
| Active Compound | % inhibition |
| 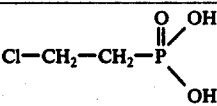<br>(known)<br>Compound 4 | 60<br><br>68 |

EXAMPLE F

Acceleration of fruit ripeness/tomato plants

Solvent: 40 parts by weight acetone
Emulsifier: 0.25 part by weight alkylarylpolyglycol ether To produce a suitable preparation of active compound, 1 part by weight of active compound was mixed with the stated amount of solvent which contained the stated amount of emulsifier, and the concentrate was diluted with a disodium hydrogen phosphate-potassium dihydrogen phosphate buffer solution (pH 6) to the desired concentration.

Green, unripe fruits of tomato plants were sprayed once with a preparation which contained 5000 ppm of active compound. An accelerated ripening of the fruits was thereby achieved.

The result can be seen from Table F.

Table F

| Acceleration of fruit ripeness / tomatoes | |
|---|---|
| Active Compound | Acceleration of ripeness in days with 5000 ppm |
| water (control) | 0 |
| 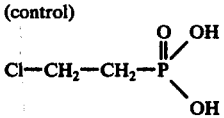<br>(known)<br>Compound 4<br>Compound 2 | 12<br><br><br>17<br>15 |

It will be seen from the above description that the invention, in one aspect, provides a plant growth regulating composition containing as active ingredient a compound according to the invention in admixture with a solid diluent or carrier containing a surface-active agent.

The invention also provides a method of regulating plant growth which comprises applying to a plant a compound according to the invention alone or in the form of a composition according to the invention in admixture with a solid or liquid diluent or carrier.

It will be understood that the specification and examples are illustrative but not limitative of the present invention and that other embodiments with the spirit and scope of the invention will suggest themselves to those skilled in the art.

What is claimed is:

1. Plant growth inhibiting composition comprising an inert plant growth regulatingly acceptable carrier, and as an active ingredient, an effective amount of a 2-chloroethane-(thiono)-phosphonic acid amido compound of the general formula

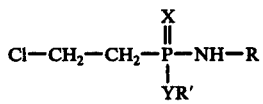

in which
X and Y, which may be the same or different, are oxygen or sulfur,
R is hydrogen or iso-propyl, and
R' is alkyl of form 1 to 4 carbon atoms, or, if R is hydrogen and Y is sulfur,
R' may additionally be phenyl which may be substituted by up to two chlorine atoms.

2. Method of inhibiting plant growth which comprises applying to a plant or its habitat a composition comprising an inert acceptable carrier, and as an active ingredient, an inhibitingly effective amount of a 2-chloroethane-(thiono)-phosphonic acid amido compound of the general formula

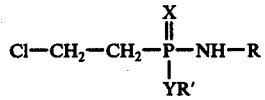

in which
X and Y, which may be the same or different, are oxygen or sulfur,
R is hydrogen or iso-propyl, and
R' is alkyl of from 1 to 4 carbon atoms, or, if R is hydrogen and R is sulfur,
R' may additionally be phenyl which may be substituted by up to two chlorine atoms.

3. Method as claimed in claim 2 wherein one of X and Y is sulfur.

4. Method as claimed in claim 2 wherein said compound is designated 2-chloroethanethiophosphonic acid-S-ethyl ester N-monoisopropylamide.

5. Method as claimed in claim 2 wherein said compound is designated 2-chloroethanethiophosphonic acid-S-phenyl ester N-monoisopropylamide.

6. Method as claimed in claim 2 wherein said compound is designated 2-chloroethanephosphonic acid isopropyl ester N-monoisopropylamide.

7. Plant growth inhibiting composition as claimed in claim 1, wherein R in the formula is hydrogen.

8. Plant growth inhibiting composition as claimed in claim 1, werein R' is phenyl substituted by chloro.

9. Plant growth inhibiting composition as claimed in claim 1, wherein both X and Y are oxygen.

10. Plant growth inhibiting composition as claimed in claim 1, wherein one of X and Y is sulfur and the other oxygen.

11. Plant growth inhibiting composition as claimed in claim 1, wherein said compound is designated 2-chloroethanephosphonic acid isopropyl ester N-monoisopropylamide.

12. Plant growth inhibiting composition as claimed in claim 1, wherein said compound is designated 2-chloroethanephosphonic acid ethyl ester N-monoisopropylamide.

13. Plant growth inhibiting composition as claimed in claim 1, wherein said compound is designated 2-chloroethanethiophosphonic acid S-ethyl ester N-monoisopropylamide.

14. Plant growth inhibiting composition as claimed in claim 1, wherein said compound is designated 2-chloroethanethiophosphonic acid S-phenyl ester N-monoisopropylamide.

15. Plant growth inhibiting composition as claimed in claim 1, wherein said compound is designated 2-chloroethanethionophosphonic acid 4'chlorophenyl ester amide.

* * * * *